(12) United States Patent
Messerli et al.

(10) Patent No.: US 7,223,292 B2
(45) Date of Patent: May 29, 2007

(54) INTERVERTEBRAL IMPLANT FOR TRANSFORAMINAL POSTERIOR LUMBAR INTERBODY FUSION PROCEDURE

(75) Inventors: Dominique Messerli, West Chester, PA (US); David Gerber, Exton, PA (US); David Paul, Phoenixville, PA (US); Kenneth Isamu Kobayashi, Exton, PA (US)

(73) Assignee: SYNTHES (U.S.A.), West Chester, PA (US)

( * ) Notice: Subject to any disclaimer, the term of this patent is extended or adjusted under 35 U.S.C. 154(b) by 0 days.

(21) Appl. No.: 11/301,759

(22) Filed: Dec. 12, 2005

(65) Prior Publication Data

US 2006/0106460 A1 May 18, 2006

Related U.S. Application Data

(63) Continuation of application No. 10/293,997, filed on Nov. 13, 2002, now Pat. No. 6,974,480, which is a continuation-in-part of application No. 09/848,178, filed on May 3, 2001, now Pat. No. 6,719,794.

(51) Int. Cl.
 *A61F 2/44* (2006.01)
(52) U.S. Cl. ............... 623/17.16; 623/17.11
(58) Field of Classification Search ... 623/17.11–17.16
See application file for complete search history.

(56) References Cited

U.S. PATENT DOCUMENTS 3,875,595 A  4/1975  Froning
4,349,921 A  9/1982  Kuntz
4,535,485 A  8/1985  Ashman et al.
4,636,217 A  1/1987  Ogilvie et al.

(Continued)

FOREIGN PATENT DOCUMENTS

EP  0 307 241  3/1989

(Continued)

OTHER PUBLICATIONS

Depuy Acromed Devex System Product Ordering Guide, Jan. 2003.

(Continued)

*Primary Examiner*—Tom Barrett
(74) *Attorney, Agent, or Firm*—Stroock & Stroock & Lavan LLP

(57) ABSTRACT

An intervertebral implant for fusing vertebrae is disclosed. The implant has a body with curved, substantially parallel posterior and anterior faces separated by, two narrow implant ends, superior and inferior faces having a plurality of undulating surfaces for contacting vertebral endplates, and at least one depression in the anterior or posterior face for engagement by an insertion tool, at least two vertical through-channels extending through the implant, a chamfer on the superior and inferior surfaces at one of the narrow implant ends, and a beveled edge along a perimeter of the superior and inferior faces. The implant configuration facilitates transforaminal insertion of the implant into a symmetric position about the midline of the spine so that a single implant provides balanced support to the spinal column. The implant may be formed of a plurality of interconnecting bodies forming a single unit. An implantation kit and method are also disclosed.

20 Claims, 19 Drawing Sheets

U.S. PATENT DOCUMENTS

| | | |
|---|---|---|
| 4,743,256 A | 5/1988 | Brantigan |
| 4,772,287 A | 9/1988 | Ray et al. |
| 4,790,297 A | 12/1988 | Luque |
| 4,820,305 A | 4/1989 | Harms et al. |
| 4,834,757 A | 5/1989 | Brantigan |
| 4,878,915 A | 11/1989 | Brantigan |
| 4,917,704 A | 4/1990 | Frey et al. |
| 4,961,740 A | 10/1990 | Ray et al. |
| 4,969,888 A | 11/1990 | Scholten et al. |
| 5,026,373 A | 6/1991 | Ray et al. |
| 5,055,104 A | 10/1991 | Ray |
| 5,059,193 A | 10/1991 | Kuslich |
| 5,071,437 A | 12/1991 | Steffee |
| 5,123,926 A | 6/1992 | Pisharodi |
| 5,192,327 A | 3/1993 | Brantigan |
| 5,222,987 A | 6/1993 | Jones |
| 5,261,913 A | 11/1993 | Marnay |
| 5,282,862 A | 2/1994 | Baker et al. |
| 5,294,391 A | 3/1994 | McMillin |
| 5,306,309 A | 4/1994 | Wagner et al. |
| 5,336,699 A | 8/1994 | Cooke et al. |
| 5,395,317 A | 3/1995 | Kambin |
| 5,397,364 A | 3/1995 | Kozak et al. |
| 5,405,402 A | 4/1995 | Dye et al. |
| 5,407,445 A | 4/1995 | Tautvydas et al. |
| 5,423,825 A | 6/1995 | Levine |
| 5,425,772 A | 6/1995 | Brantigan |
| 5,429,863 A | 7/1995 | McMillin |
| 5,443,514 A | 8/1995 | Steffee |
| 5,458,638 A | 10/1995 | Kuslich et al. |
| 5,458,642 A | 10/1995 | Beer et al. |
| 5,474,555 A | 12/1995 | Puno et al. |
| 5,476,880 A | 12/1995 | Cooke et al. |
| 5,480,442 A | 1/1996 | Bertagnoli |
| 5,489,307 A | 2/1996 | Kuslich et al. |
| 5,489,308 A | 2/1996 | Kuslich et al. |
| 5,514,180 A | 5/1996 | Heggeness et al. |
| 5,522,899 A | 6/1996 | Michelson |
| 5,562,736 A | 10/1996 | Ray et al. |
| 5,571,103 A | 11/1996 | Bailey |
| 5,609,635 A | 3/1997 | Michelson |
| 5,609,636 A | 3/1997 | Kohrs et al. |
| 5,618,286 A | 4/1997 | Brinker |
| 5,645,596 A | 7/1997 | Kim et al. |
| 5,658,335 A | 8/1997 | Allen |
| 5,669,909 A | 9/1997 | Zdeblick et al. |
| 5,674,295 A | 10/1997 | Ray et al. |
| 5,676,146 A | 10/1997 | Scarborough |
| 5,683,463 A | 11/1997 | Godefroy et al. |
| 5,683,464 A | 11/1997 | Wagner et al. |
| 5,709,685 A | 1/1998 | Dombrowski et al. |
| 5,716,415 A | 2/1998 | Steffee |
| 5,741,261 A | 4/1998 | Moskovitz et al. |
| 5,755,797 A | 5/1998 | Baumgartner |
| 5,766,252 A | 6/1998 | Henry et al. |
| 5,782,919 A | 7/1998 | Zdeblick et al. |
| 5,820,918 A | 10/1998 | Ronan et al. |
| 5,824,077 A | 10/1998 | Mayer |
| 5,824,094 A | 10/1998 | Serhan et al. |
| 5,860,973 A | 1/1999 | Michelson |
| 5,865,845 A | 2/1999 | Thalgott |
| 5,865,846 A | 2/1999 | Bryan et al. |
| 5,868,745 A | 2/1999 | Alleyne |
| 5,876,457 A | 3/1999 | Picha et al. |
| 5,885,300 A | 3/1999 | Tokuhashi et al. |
| 5,888,224 A | 3/1999 | Beckers et al. |
| 5,888,227 A | 3/1999 | Cottle |
| 5,897,593 A | 4/1999 | Kohrs et al. |
| 5,904,719 A | 5/1999 | Errico et al. |
| 5,913,896 A | 6/1999 | Boyle et al. |
| 5,919,235 A | 7/1999 | Husson et al. |
| 5,954,724 A | 9/1999 | Davidson |
| 5,961,554 A | 10/1999 | Janson et al. |
| 5,984,922 A | 11/1999 | McKay |
| 5,989,289 A | 11/1999 | Coates et al. |
| 6,019,793 A | 2/2000 | Perren et al. |
| 6,025,538 A | 2/2000 | Yaccarino, III |
| 6,033,438 A | 3/2000 | Bianchi et al. |
| 6,039,762 A | 3/2000 | McKay |
| 6,042,582 A | 3/2000 | Ray |
| 6,059,790 A | 5/2000 | Sand et al. |
| 6,059,829 A | 5/2000 | Schläpfer et al. |
| 6,074,423 A | 6/2000 | Lawson |
| 6,080,158 A | 6/2000 | Lin |
| 6,086,613 A | 7/2000 | Camino et al. |
| 6,113,602 A | 9/2000 | Sand |
| 6,113,638 A | 9/2000 | Williams et al. |
| 6,136,031 A | 10/2000 | Middleton |
| 6,143,032 A | 11/2000 | Schafer et al. |
| 6,143,033 A | 11/2000 | Paul et al. |
| 6,156,040 A | 12/2000 | Yonemura et al. |
| 6,159,211 A | 12/2000 | Boriani et al. |
| 6,159,212 A | 12/2000 | Schoedinger et al. |
| 6,174,311 B1 | 1/2001 | Branch et al. |
| 6,200,347 B1 | 3/2001 | Anderson et al. |
| 6,241,769 B1 | 6/2001 | Nicholson et al. |
| 6,245,108 B1 | 6/2001 | Biscup |
| 6,261,586 B1 | 7/2001 | McKay |
| 6,296,664 B1 | 10/2001 | Middleton |
| 6,315,797 B1 | 11/2001 | Middleton |
| 6,342,074 B1 | 1/2002 | Simpson |
| 6,350,283 B1 | 2/2002 | Michelson |
| 6,371,988 B1 | 4/2002 | Pafford et al. |
| 6,387,130 B1 | 5/2002 | Stone et al. |
| 6,395,035 B2 | 5/2002 | Bresina et al. |
| 6,423,095 B1 | 7/2002 | Van Hoeck et al. |
| 6,432,106 B1 | 8/2002 | Fraser |
| 6,447,544 B1 | 9/2002 | Michelson |
| 6,454,805 B1 | 9/2002 | Baccelli et al. |
| 6,458,159 B1 | 10/2002 | Thalgott |
| 2001/0008980 A1 | 7/2001 | Gresser et al. |
| 2001/0012966 A1 | 8/2001 | Studer et al. |
| 2001/0016774 A1 | 8/2001 | Bresina et al. |
| 2001/0016777 A1 | 8/2001 | Biscup |
| 2001/0031967 A1 | 10/2001 | Nicholson et al. |
| 2002/0004683 A1 | 1/2002 | Michelson |
| 2002/0013624 A1 | 1/2002 | Michelson |
| 2002/0019637 A1 | 2/2002 | Frey et al. |
| 2002/0022886 A1 | 2/2002 | Fuss et al. |
| 2002/0026243 A1 | 2/2002 | Lin |
| 2002/0055781 A1 | 5/2002 | Sazy |
| 2002/0065558 A1 | 5/2002 | Varga et al. |
| 2002/0065560 A1 | 5/2002 | Varga et al. |
| 2002/0077700 A1 | 6/2002 | Varga et al. |
| 2002/0082597 A1 | 6/2002 | Fraser |
| 2002/0087212 A1 | 7/2002 | James et al. |
| 2002/0091447 A1 | 7/2002 | Shimp et al. |
| 2002/0099376 A1 | 7/2002 | Michelson |
| 2002/0099444 A1 | 7/2002 | Boyd et al. |
| 2002/0107573 A1 | 8/2002 | Steinberg |
| 2002/0165550 A1* | 11/2002 | Frey et al. .......... 606/85 |

FOREIGN PATENT DOCUMENTS

| | | |
|---|---|---|
| EP | 0 551 574 | 7/1993 |
| EP | 0 559 419 A2 | 12/1993 |
| EP | 0 834 295 | 4/1998 |
| EP | 0 916 323 A1 | 5/1999 |
| FR | 2 736 537 | 12/1995 |
| FR | 2 724 312 | 3/1996 |
| FR | 2 727 003 | 5/1996 |
| FR | 2 727 004 | 5/1996 |
| FR | 2 727 005 | 5/1996 |
| FR | 2 736 538 | 1/1997 |

| | | |
|---|---|---|
| JP | 8010275 | 1/1996 |
| JP | 8010276 | 1/1996 |
| JP | 9122160 | 5/1997 |
| JP | 2001170092 | 6/2001 |
| WO | WO 89/09035 | 10/1989 |
| WO | WO 96/25086 | 8/1996 |
| WO | WO 96/40014 | 12/1996 |
| WO | WO 97/15248 | 5/1997 |
| WO | WO 99/09914 | 3/1999 |
| WO | WO 99/37255 | 7/1999 |
| WO | WO 00/07527 | * 2/2000 |
| WO | WO 00/74608 | 12/2000 |
| WO | WO 01/28469 A2 * | 4/2001 |
| WO | WO 01/28469 A3 | 4/2001 |
| WO | WO 01/70144 A1 | 9/2001 |
| WO | WO 01/95838 A1 | 12/2001 |

OTHER PUBLICATIONS

Regeneration Technologies, Inc. Catalog, Nov. 1999.
Sofamor Danek Surgical Technique for Tangent Posterior Discectomy & Grafting Instrumentation Set, 1999.

* cited by examiner

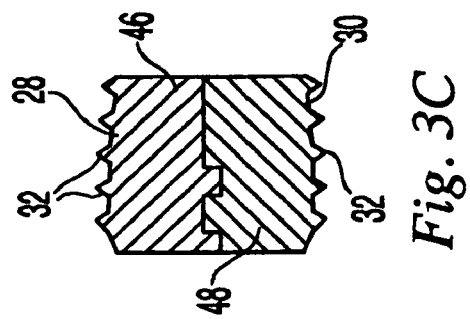
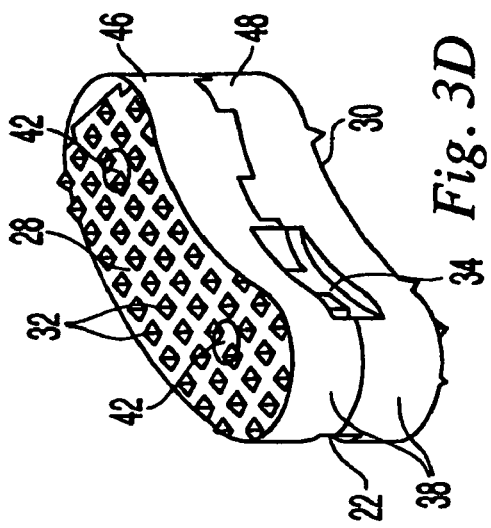
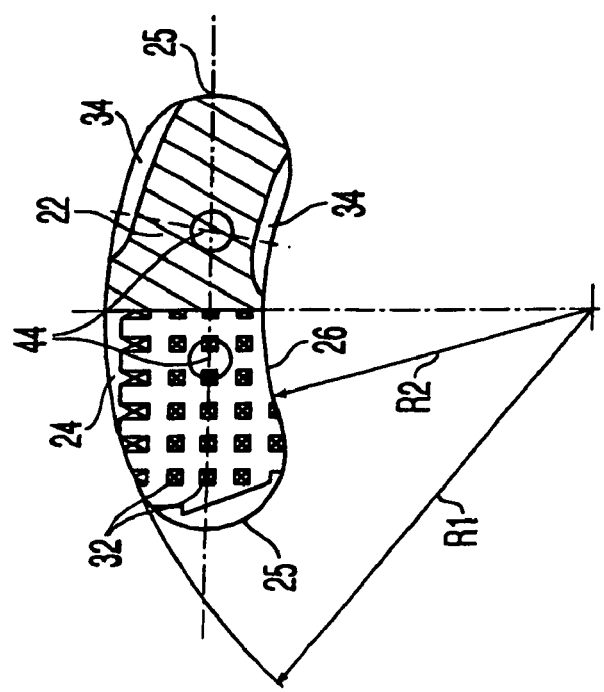
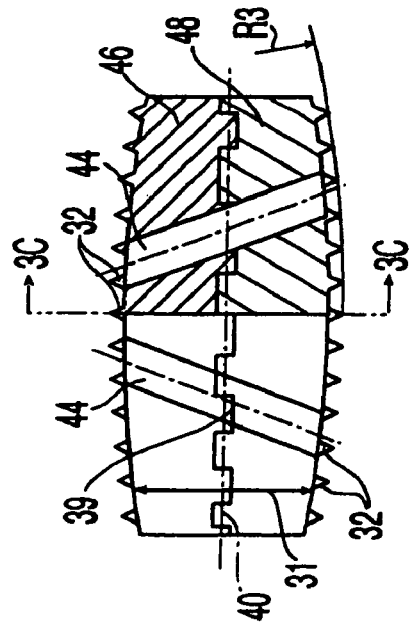
Fig. 3C
Fig. 3D
Fig. 3A
Fig. 3B

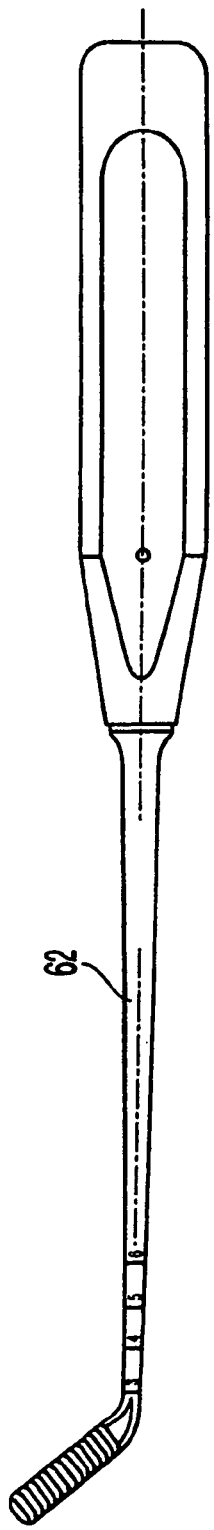
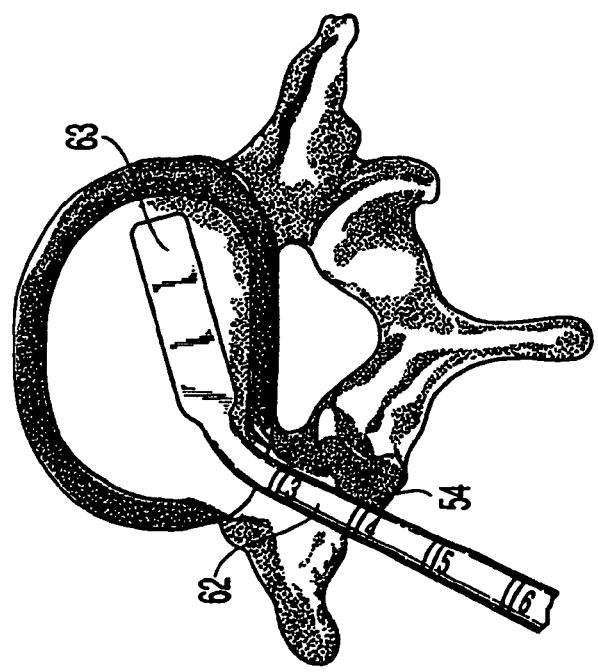
Fig. 9A
Fig. 9B

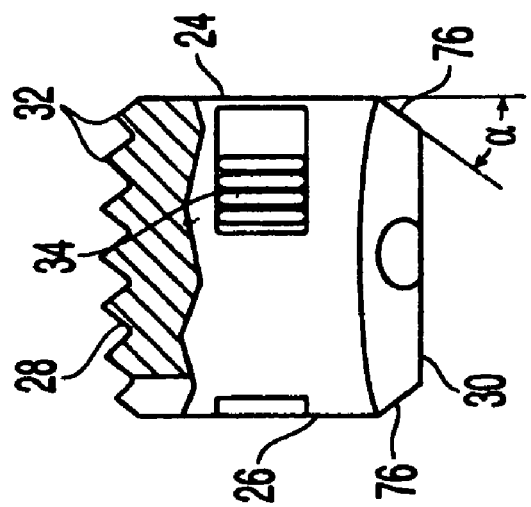
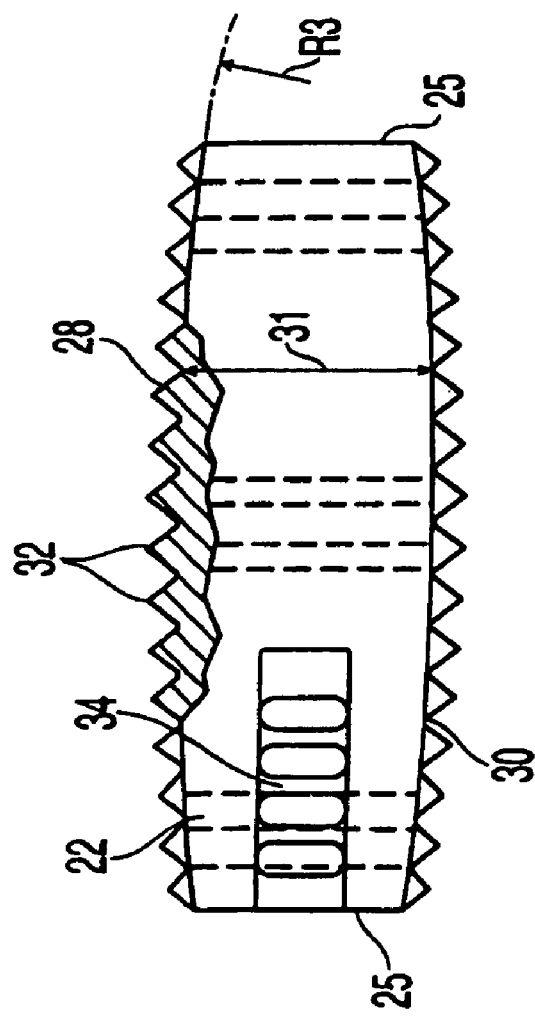
Fig. 16B
Fig. 16A

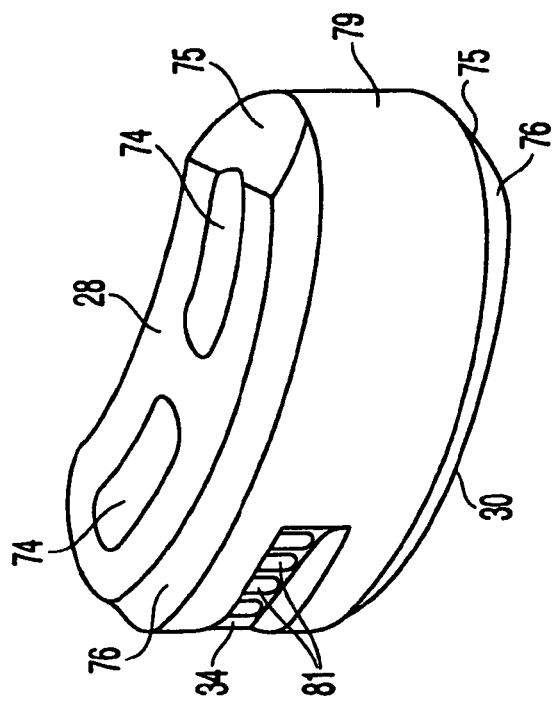
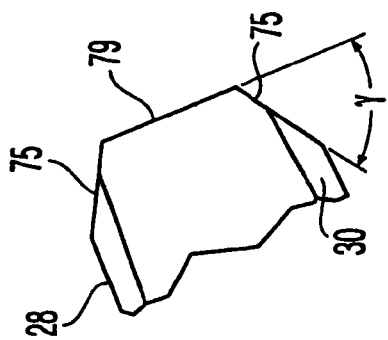
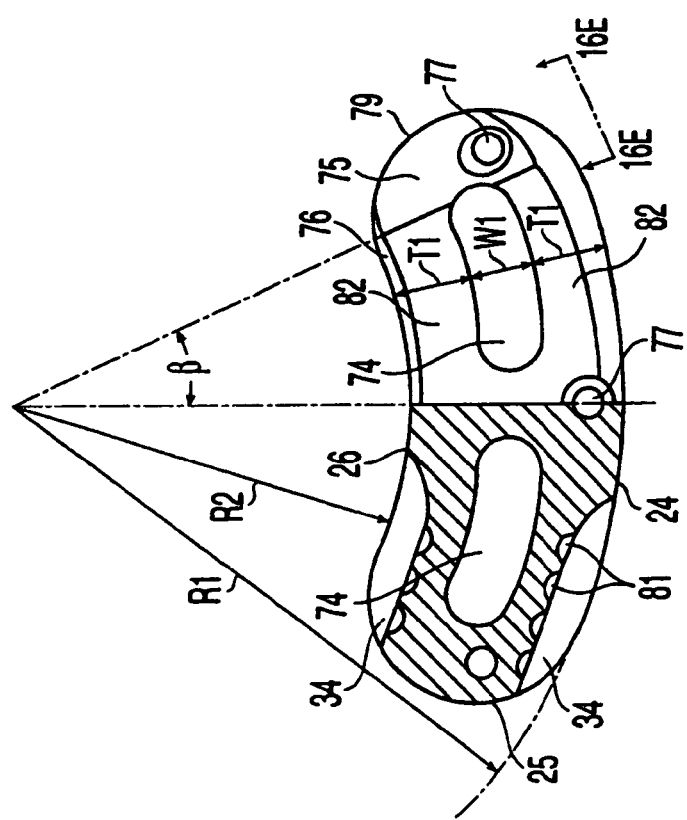
Fig. 16D
Fig. 16E
Fig. 16C

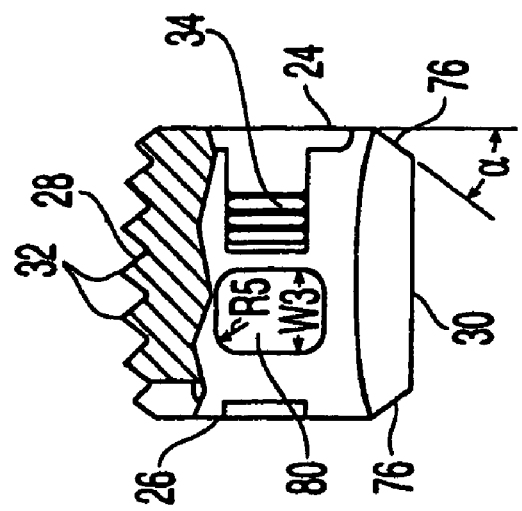
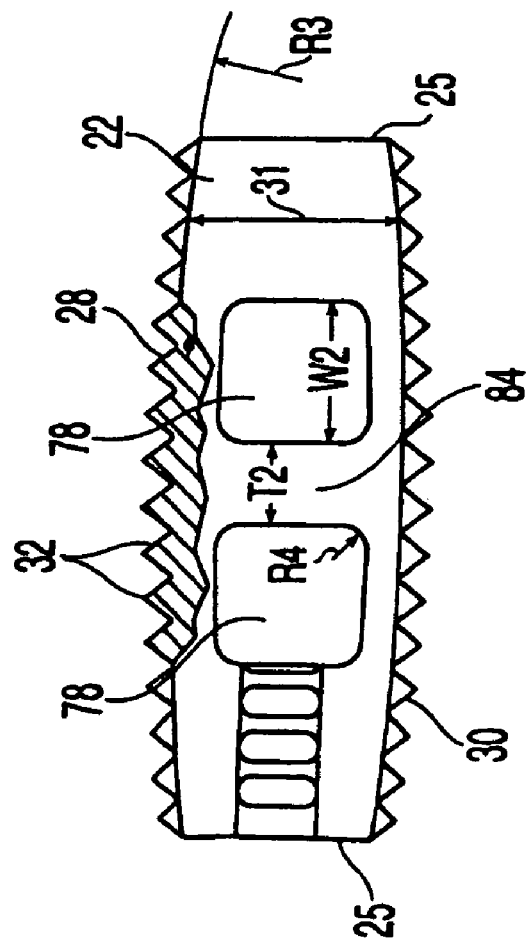

INTERVERTEBRAL IMPLANT FOR TRANSFORAMINAL POSTERIOR LUMBAR INTERBODY FUSION PROCEDURE

CROSS-REFERENCE TO RELATED APPLICATIONS

This application is a continuation of U.S. patent application Ser. No. 10/293,997, filed Nov. 13, 2002, now U.S. Pat. No. 6,974,480, which is a continuation-in-part of U.S. patent application Ser. No. 09/848,178, filed May 3, 2001, now U.S. Pat. No. 6,719,794.

FIELD OF THE INVENTION

The present invention is directed to an intervertebral implant, its accompanying instrumentation and their method of use. More particularly, the present invention is directed to an intervertebral implant and instrumentation for use in a transforaminal posterior lumbar interbody fusion procedure.

BACKGROUND OF THE INVENTION

A number of medical conditions such as compression of spinal cord nerve roots, degenerative disc disease, herniated nucleus pulposus, spinal stenosis and spondylolisthesis can cause severe low back pain. Intervertebral fusion is a surgical method of alleviating low back pain. In posterior lumbar interbody fusion ("PLIF"), two adjacent vertebral bodies are fused together by removing the affected disc and inserting posteriorly one or more implants that would allow for bone to grow between the two vertebral bodies to bridge the gap left by the removed disc.

One variation of the traditional PLIF technique is the transforaminal posterior lumbar interbody fusion (T-PLIF) technique. Pursuant to this procedure, an implant is inserted into the affected disc space via a unilateral (or sometimes bilateral), posterior approach, offset from the midline of the spine, by removing portions of the facet joint of the vertebrae. The T-PLIF approach avoids damage to nerve structures such as the dura, cauda equina and the nerve root, but the resulting transforaminal window available to remove the affected disc, prepare the vertebral endplates, and insert the implant is limited laterally by soft tissue and medially by the cauda equina.

A number of different implants typically used for the traditional PLIF procedure have been used for the T-PLIF procedure with varying success. These include threaded titanium or polymer cages, allograft wedges, rings, etc. However, as these devices were not designed specifically for the T-PLIF procedure, they are not shaped to be easily insertable into the affected disc space through the narrow transforaminal window, and may require additional retraction of the cauda equina and nerve roots. Such retraction can cause temporary or permanent nerve damage. In addition, some of these implants, such as the threaded titanium or polymer cage, suffer from the disadvantage of requiring drilling and tapping of the vertebral endplates for insertion. Further, the incidence of subsidence in long term use is not known for such cages. Finally, restoration of lordosis, i.e., the natural curvature of the lumbar spine is very difficult when a cylindrical or square titanium or polymer cage is used.

As the discussion above illustrates, there is a need for an improved implant and instrumentation for fusing vertebrae via the transforaminal lumbar interbody fusion procedure.

SUMMARY OF THE INVENTION

The present invention relates to an intervertebral implant ("T-PLIF implant") and its use during a transforaminal lumbar interbody fusion procedure. In a preferred embodiment, the T-PLIF implant has an arcuate body with curved, preferably substantially parallel, posterior and anterior faces separated by two narrow implant ends, and superior and inferior faces having textured surfaces for contacting upper and lower vertebral endplates. Preferably, the textured surfaces comprise undulating structures which may include projections, such as teeth, of a saw-tooth or pyramidal configuration, or ridges which preferably penetrate the vertebral endplates and prevent slippage. The narrow implant ends may be rounded or substantially flat. The arcuate implant configuration facilitates insertion of the implant via a transforaminal window. The implant, which may be formed of allogenic bone, metal, or plastic, may also have at least one depression, such as a channel or groove, in the posterior or anterior face for engagement by an insertion tool, such as an implant holder. In a preferred aspect, the superior and inferior faces are convex, and the thickness of the implant tapers with its greatest thickness in the middle region between the narrow ends of the implant, i.e., at a section parallel to a sagittal plane, and decreasing toward each of the narrow ends.

In another embodiment, the T-PLIF implant preferably has curved, substantially parallel posterior and anterior faces extending along a longitudinal axis of the implant, a pair of convex narrow ends separating the posterior and anterior faces, a chamfer on the superior and inferior faces at one of the convex narrow ends, a beveled edge along a perimeter of the superior and inferior faces, and at least one depression in the anterior or posterior face for engagement by an insertion tool, where the superior and inferior faces contact upper and lower vertebral endplates and define a thickness of the implant. The T-PLIF implant preferably has at least two vertical through-channels extending through the implant from the superior face to the inferior face, each vertical through-channel having a width and walls on posterior and anterior sides of the width. The arcuate implant configuration and the chamfer on the inferior and superior faces at the narrow insertion end of the implant facilitate insertion of the implant via the transforaminal window. In a preferred aspect, the implant also has at least two anterior-posterior horizontal through-channels extending through the implant from the posterior face to the anterior face. The implant may also feature at least one lateral horizontal through-channel extending from a narrow end of the implant inward toward an adjacent anterior-posterior horizontal through-channel. Each of the channels may be packed with bone-graft and/or bone growth inducing material to aid in spinal fusion. In one exemplary embodiment, the walls on the posterior and anterior sides of the width of the vertical through-channels have a thickness greater than the width of the vertical through channels. The implant may be formed of a radiolucent polymer material selected from the polyaryl ether ketone family (PAEK), such as polyether ether ketone (PEEK) or polyether ketone ketone (PEKK), or other suitable biocompatible material of sufficient strength, such as titanium. The implant may include one or more radiopaque marker, such as pins or screws, extending substantially through the thickness of the implant to indicate implant location and size in postoperative spinal scans.

In another preferred embodiment, the implant is formed of a plurality of interconnecting bodies assembled to form a single unit. In this configuration, the plurality of interconnecting bodies forming the T-PLIF implant may be press-fit together and may include one or more pin(s) or screw(s) extending through an opening in the plurality of bodies to hold the bodies together as a single unit. Adjacent surfaces of the plurality of bodies may also have mating interlocking surfaces that aid in holding the bodies together as a single unit.

In still another preferred embodiment, the present invention relates to a kit for implanting an intervertebral implant into an affected disc space of a patient via a transforaminal window. The kit includes an implant having an arcuate body with curved, preferably substantially parallel, posterior and anterior faces separated by two narrower implant ends, superior and inferior faces preferably having a textured surface, such as projections or teeth, for contacting and preferably penetrating upper and lower vertebral endplates. The superior and inferior faces may define a thickness. Preferably the implant has at least one depression in its posterior or anterior face near one of its ends for engagement by an insertion tool. The implant may also have two or more vertical through-channels extending through the implant from the superior face to the inferior face, each vertical through-channel having a width and walls on posterior and anterior sides of the width, a chamfer on the superior and inferior surfaces at an insertion end and a beveled edge along a perimeter of the superior and inferior faces. The kit may further include one or more trial-fit spacer(s) for determining the appropriate size of the implant needed to fill the affected disc space; an insertion tool having an angled or curved neck for holding and properly positioning the implant during insertion through the transforaminal window, and an impactor having an angled or curved neck for properly positioning the implant within the affected disc space. The face of the impactor may be concavely shaped to mate with the narrow end of the T-PLIF implant during impaction. The kit may further include a lamina spreader for distracting vertebrae adjacent to the affected disc space, an osteotome for removing facets of the vertebrae adjacent to the affected disc space to create a transforaminal window, one or more curettes, angled and/or straight, for removing disc material from the affected disc space, a bone rasp for preparing endplates of the vertebrae adjacent the affected disc space, and a graft implant tool for implanting bone graft material into the affected disc space. The kit may still further include a curved guide tool to guide the implant into the affected disc space. In another preferred embodiment, the implant of the kit includes two or more anterior-posterior horizontal through-channels extending through the implant from the posterior face to the anterior face, wherein a portion of the walls on the posterior and anterior sides of the width of the vertical through-channels of the implant may have a thickness greater than the width of the vertical through channels. The implant of the kit may also include one or more lateral horizontal through-channel(s) extending from a narrow end of the implant inward toward an adjacent anterior-posterior horizontal through-channel. Each of the channels may be packed with bone-graft and/or bone growth inducing material prior to and/or after insertion to aid in spinal fusion. The implant may also include one or more radiopaque markers, such as pins, that extend substantially through the thickness of the implant.

In yet another aspect, a method for implanting an intervertebral implant into an affected disc space of a patient via a transforaminal window is described. The transforaminal window is created, the disc space is prepared and bone graft material may be inserted into the affected disc space. Using an insertion tool, an implant is inserted into the affected disc space via the transforaminal window and seated in a portion of the disc space closer to the anterior edge of the disc space than the posterior edge of the disc space. As discussed above, the implant preferably has an arcuate body with curved, substantially parallel posterior and anterior faces separated by two narrow implant ends, superior and inferior faces having a plurality of undulating surfaces for contacting upper and lower vertebral endplates, and preferably at least one depression at a first end for engagement by the insertion tool. In the present method, the arcuate implant configuration facilitates insertion of the implant via the transforaminal window. The implant may be inserted along an arcuate path. The method may further comprise impacting the implant with an impactor tool to properly position the implant within the affected disc space. Either or both the insertion tool and the impactor tool may be angled to facilitate insertion, alignment, placement and/or proper seating of the implant. The implant may also feature two or more vertical through-channel(s) extending through the implant from the superior face to the inferior face, each vertical through-channel having a width and walls on posterior and anterior sides of the width, a chamfer on the superior and inferior faces at the insertion end, and a beveled edge along a perimeter of the superior and inferior faces. The implant may also have two or more anterior-posterior horizontal through-channel(s) extending through the implant from the posterior face to the anterior face and/or at least one lateral horizontal through-channel extending from a narrow end of the implant inward toward an adjacent anterior-posterior horizontal through-channel. Each of the channels may be packed with bone-graft and/or bone growth inducing material before implantation and/or after implantation to aid in spinal fusion.

BRIEF DESCRIPTION OF THE DRAWINGS

FIG. 3A is a partial cross-section view of another embodiment of an implant according to the present invention;

FIG. 3B is a partial cross-section view along the longer axis of the implant of FIG. 3A;

FIG. 3C is a cross-section view taken along line 3C—3C of FIG. 3B;

FIG. 3D is a perspective view of the implant of FIG. 3A;

FIG. 9A depicts an angled bone rasp for use during a T-PLIF procedure;

FIG. 9B depicts an angled bone rasp removing material from an affected disc space;

FIG. 16A is a partial cross-section side view along the longer axis of still another embodiment of an implant according to the present invention;

FIG. 16B is a partial cross-section side view along the shorter axis of the implant of FIG. 16A;

FIG. 16C is a partial cross-section top view of the implant of FIG. 16A;

FIG. 16D is a perspective view of the implant in FIG. 16A;

FIG. 16E is a partial side view of the implant taken along line 16E—16E in FIG. 16C;

FIG. 17A is a partial cross-section side view along the longer axis of still another embodiment of an implant according to the present invention;

FIG. 17B is a partial cross-section side view along the shorter axis of the implant of FIG. 17A;

DESCRIPTION OF THE PREFERRED EMBODIMENTS

While various descriptions of the present invention are provided below, it should be understood that these descriptions are intended to illustrate the principals of the present invention and its various features, which can be used singly or in any combination thereof. Therefore, this invention is not to be limited to only the specifically preferred embodiments described and depicted herein.

Figure 1:
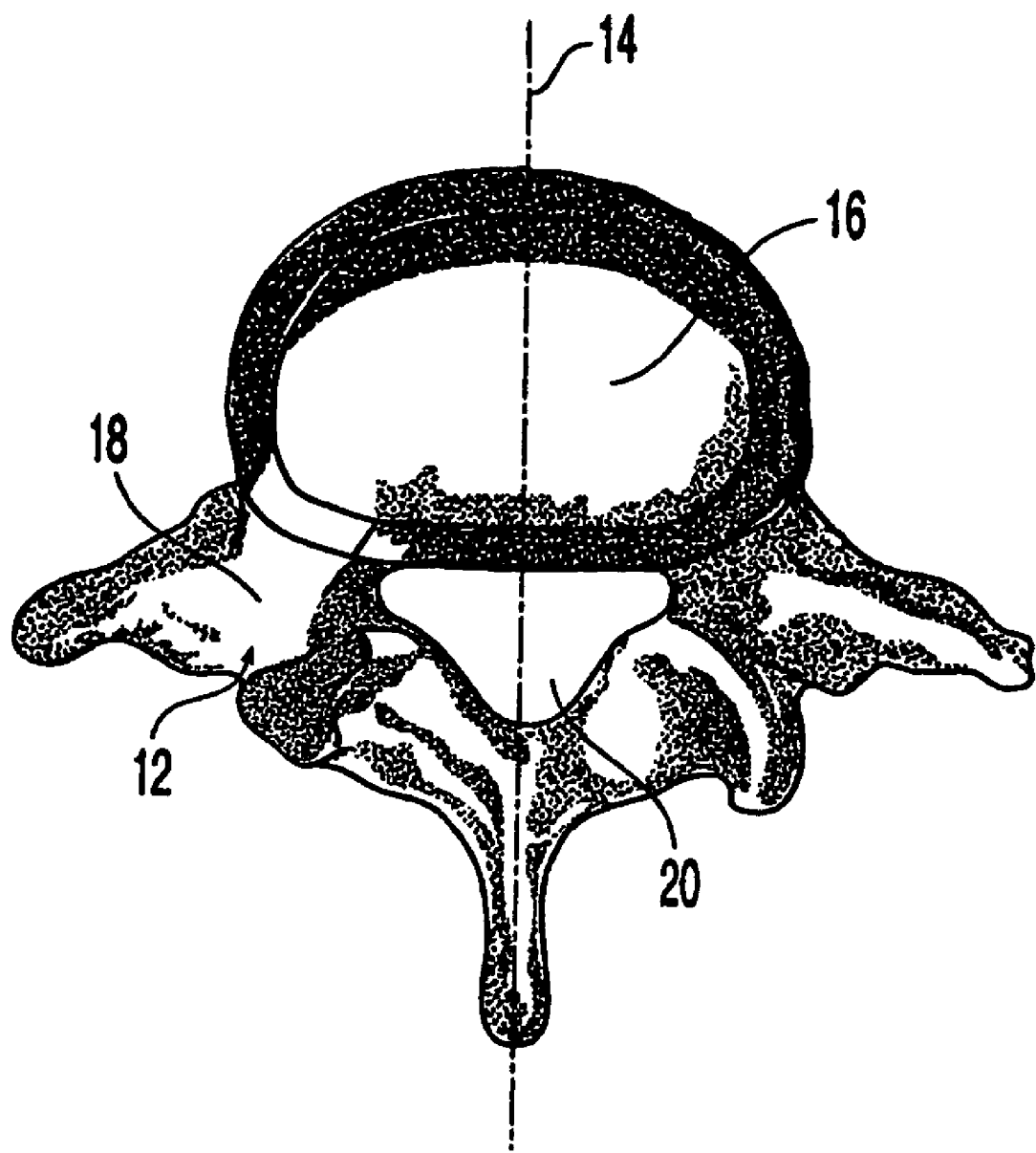
FIG. 1 is a top view of a typical human vertebrae showing the transforaminal window through which an implant according to the present invention is inserted.

The transforaminal posterior lumbar interbody fusion implant ("T-PLIF implant") is designed for use as an intervertebral spacer in spinal fusion surgery where an affected disk is removed from between two adjacent vertebrae and replaced with an implant that provides segmental stability and allows for bone to grow between the two vertebrae to bridge the gap created by disk removal. Specifically, the T-PLIF implant is designed for the transforaminal lumbar interbody fusion (T-PLIF) technique, which, as shown in FIG. 1, involves a posterior approach 12, offset from the midline 14 of the spine, to the affected intervertebral disk space 16. The window 18 available for implant insertion using the T-PLIF technique is limited medially by the dura or cauda equina 20 and the superior exiting nerve root (not shown).

As shown in FIGS. 2A through 2D, in a preferred embodiment, the T-PLIF implant has an arcuate, "rocker-like" body 22 with curved anterior and posterior faces 24, 26 to facilitate the offset insertion of the implant through the narrow approach window 18 into the disk space. Preferably, the anterior and posterior faces 24 and 26 are substantially parallel, separated by a pair of narrow ends 25. Narrow ends 25 may be rounded or blunt. The superior and inferior surfaces 28, 30 preferably have projections, such as teeth 32, for engaging the adjacent vertebrae. Teeth 32 on superior and inferior surfaces 28, 30 preferably provide a mechanical interlock between implant 22 and the end plates by penetrating the end plates. The initial mechanical stability afforded by teeth 32 minimizes the risk of post-operative expulsion/slippage of implant 22. Teeth 32 may have a saw-tooth shape, where one side of the tooth is perpendicular to the superior or inferior surface, or a pyramid shape, where each tooth has four sides and forms an acute angle with the superior or inferior face. Preferably, implant body 22 has at least one channel or slot 34 on one end of implant 22 for engagement by a surgical instrument, such as an implant holder 66 (shown in FIG. 11A). It should be noted that implant 22 may also be configured with a channel 34 on only one side or without channels altogether. Other known methods for engaging the implant with surgical instruments, such as a threaded bore for receiving the threaded end of a surgical tool or a non-threaded bore for receiving an expandable head of an insertion tool, may also be used.

Figure 2C:
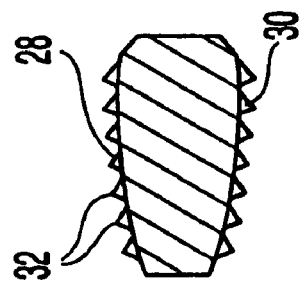
FIG. 2C is a cross-section view taken along line 2C—2C of FIG. 2B.
Figure 2D:
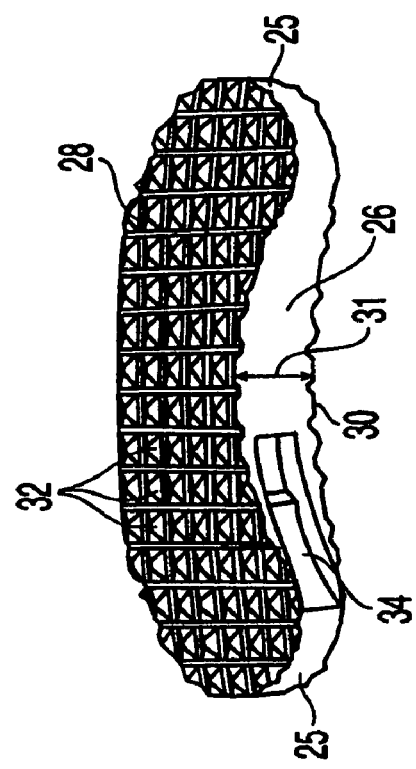
FIG. 2D is a perspective view of the implant of FIG. 2A.
Figure 2A:
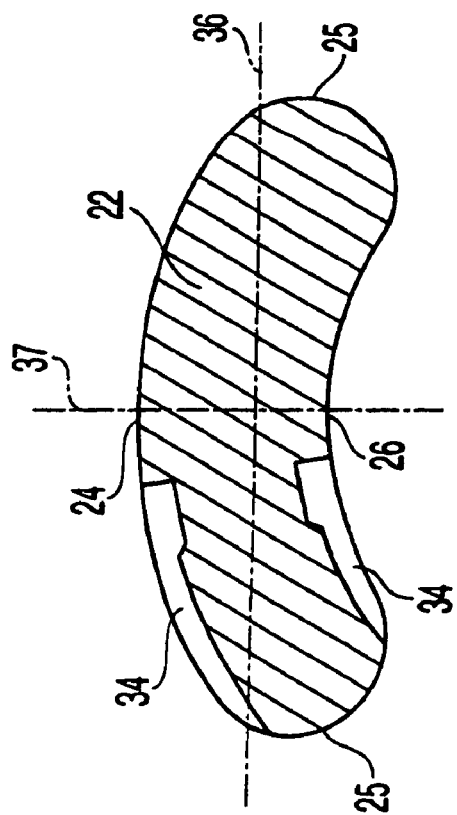
FIG. 2A is a cross-section view of an embodiment of an implant according to the present invention.
Figure 2B:
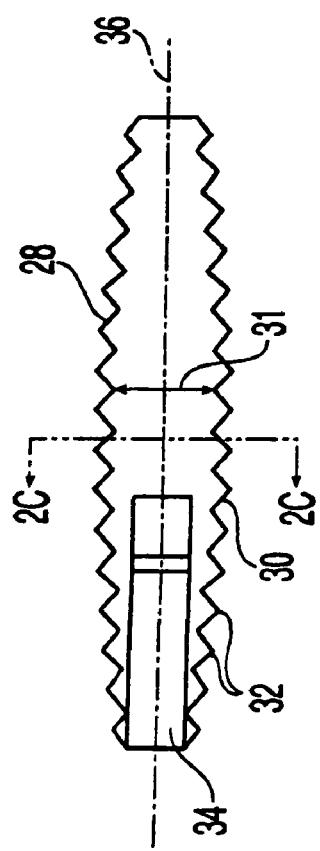
FIG. 2B is a side view along the longer axis of the implant of FIG. 2A.

As shown in FIG. 2B, thickness 31 of implant 22 is greatest at the mid-section between the two narrow implant ends 25 and tapers gradually along the longitudinal axis 36 of implant 22 so that it is thinnest at the narrow ends 25 of implant 22. The taper is preferably arcuate and provides a convex configuration and a proper anatomical fit, while also facilitating insertion of implant 22 into the affected disc space. It should be noted that in a preferred embodiment, thickness 31 does not taper or change along the shorter axis 37 of implant 22. Thus for any given cross section taken perpendicular to the longitudinal axis 36 of the implant, the distance between the superior and inferior surfaces 28 and 30 remains substantially constant. In alternate embodiments, however, thickness 31 may change or taper along shorter axis 37 of implant 22. The dimensions of implant 22 can be varied to accommodate a patient's anatomy, and the thickness of the implant is chosen based on the size of the disk space to be filled. Preferably, implant 22 has a maximum thickness 31 at its mid-section of about 7.0 to about 17.0 mm, and may be formed of metal, allograft, a metal-allograft composite, a carbon-fiber polymer, pure polymer or plastic or combinations of these materials. The implant may also be formed of a resorbable polymer. The thickness at the narrow ends 25 of implant 22 may range from about 1.5 to about 2.0 mm less than the maximum thickness at the mid-section. The implant may range from about 26 to about 32 mm in length, and have a width from about 9 to 11 mm. Implant 22, which as shown most clearly in FIG. 2A is symmetric about at least one axis of rotation 37, is intended for symmetric placement about the midline 14 of the spine (see FIG. 19). The arcuate configuration of implant 22 facilitates insertion of the implant from the transforaminal approach into a symmetric position about the midline of the spine so that a single implant provides balanced support to the spinal column.

As shown in FIGS. 3A–3D, in an alternate embodiment implant 22 may be formed of two or more pieces 38 preferably having interlocking grooves 39 and pallets 40 that may be press-fit and fastened together with pins or screws 42. The number and orientation of pins or screws 42 can be varied. In addition or alternatively, the pieces may be fastened using glue, cement or a welding or bonding process. This multi-component configuration may be particularly useful for implants formed of allograft bone, since it may be difficult and/or impractical to obtain a single, sufficiently large piece of allograft for some applications. In the case of implants formed completely of artificial (i.e., non-allograft) materials, such as steel, plastic or metallic or non-metallic polymer, a one-piece implant may be more practical. As shown in FIG. 3C, in a preferred embodiment for any given cross-section taken perpendicular to the longitudinal axis of the implant, the distance between the superior and inferior surfaces 28 and 30 remains substantially constant.

As in the previous embodiment, the anterior and posterior faces 24, 26 are preferably substantially parallel, and, as shown, may be defined by radii of curvature R1 and R2, where R1, for example, may be in the range of 25–35 mm and preferably about 28 mm and R2, for example, may be in the range of 15 to 25 mm and preferably about 19 mm. The superior and inferior surfaces 28, 30 are arcuate shaped and the implant has a thickness 31, which is preferably greatest at a center portion between narrow ends 25 and gradually tapers becoming thinnest at narrow ends 25. Tapering thickness 31 may be defined by a radius of curvature R3, where R3 for example, may be in the range of 85 to 115 mm and preferably about 100 mm. As shown, the component pieces 46, 48 of implant 22 have holes 44 to accommodate pins or screws 42. Holes 44 are preferably drilled after component pieces 38 have been stacked one on top of the other. The multiple pieces 38 are then assembled with screws or pins 42 so that practitioners receive the implant 22 as a single, pre-fabricated unit. The upper component piece 46 has an arcuate superior surface preferably with teeth 32, while its bottom surface is preferably configured with grooves and pallets preferably to interlock with the upper surface of lower component piece 48. The arcuate inferior surface 30 of lower component piece 48 also preferably has teeth 32 for engaging the lower vertebral endplate of the affected disc space. Either or both superior and inferior surfaces 28, 30 may have ridges, texturing or some other form of engaging projection in place of teeth 32.

Figure 17D:
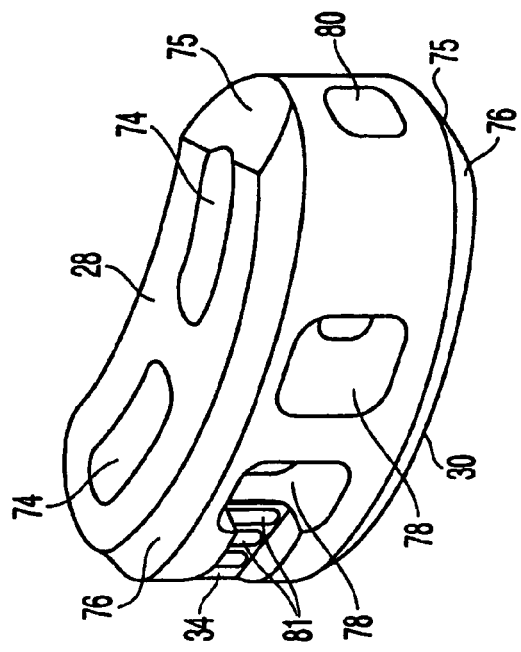
FIG. 17D is a perspective view of the implant in FIG. 17A.
Figure 17E:
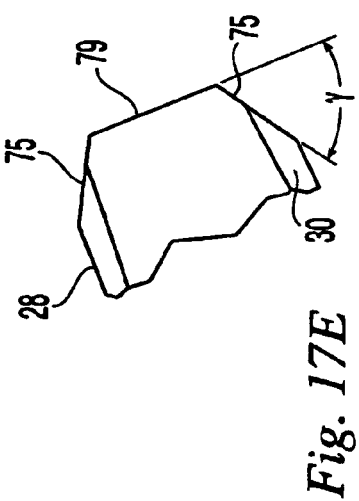
FIG. 17E is a partial side view of the implant taken along line 17E—17E in FIG. 17C.

Reference is now made to FIGS. 16A–16E, which display still another preferred embodiment of the implant of the present invention. Similar in profile to the embodiments shown in FIGS. 2A and 3A, the anterior and posterior faces 24, 26 are substantially parallel, and, as shown, may be defined by radii of curvature R1 and R2, where R1, for example, may be in the range of 25 to 35 mm and preferably about 29 mm and R2, for example, may be in the range of 15 to 25 mm and preferably about 19 mm. The superior and inferior surfaces 28, 30 are arcuate shaped and the implant has a thickness 31, which is preferably greatest at a center portion between narrow ends 25 and gradually tapers becoming thinnest at narrow ends 25. Tapering thickness 31 may be defined by a radius of curvature R3, where R3 for example, may be in the range of 85 to 115 mm and preferably about 100 mm. Superior and inferior surfaces 28, 30 preferably have a textured surface which may include a plurality of undulating surfaces, such as, for example, teeth 32, for engaging the upper and lower vertebral endplates of the affected disc space. (Note: For sake of clarity, teeth 32 are not pictured in FIGS. 16C–16E, 17C–17E or on the inferior face of the implant shown in FIGS. 16B & 17B.)

Figure 11A:
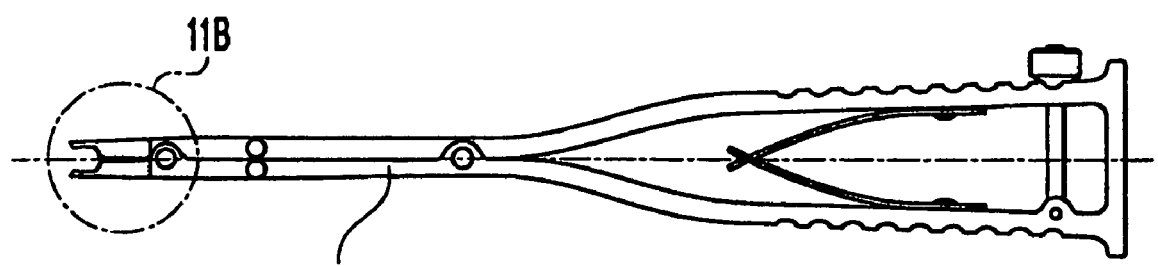
FIG. 11A depicts an implant holder for use during a T-PLIF procedure.
Figure 11B:
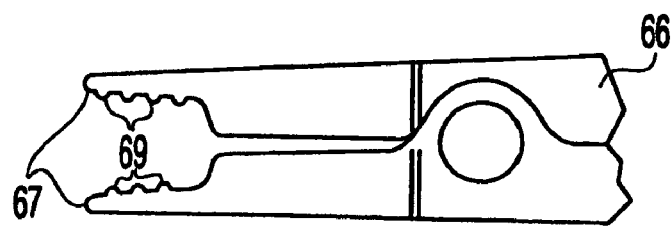
FIG. 11B depicts the tips of the implant holder shown in FIG. 11A.
Figure 17C:
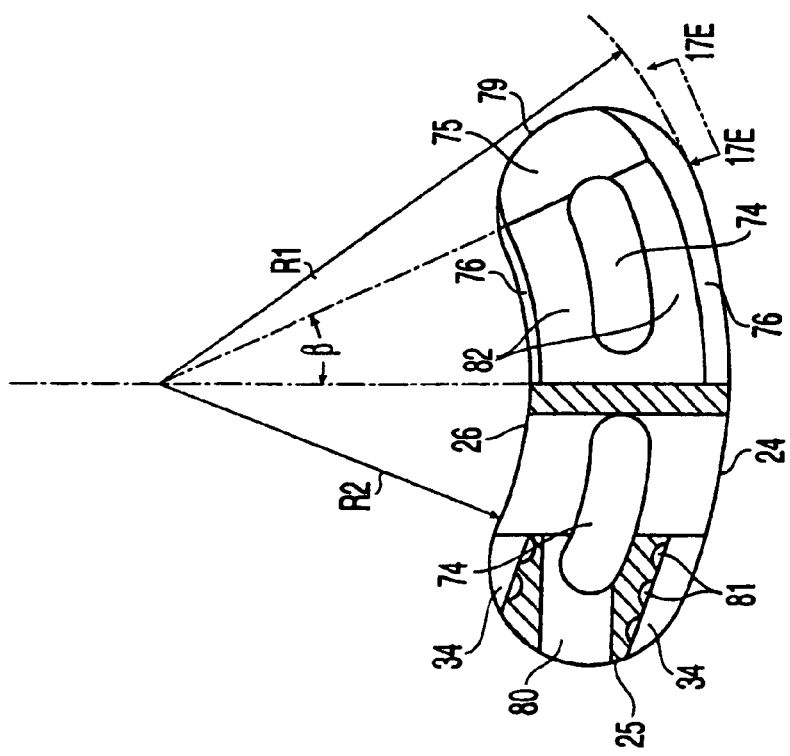
FIG. 17C is a partial cross-section top view of the implant of FIG. 17A.

As shown, the implant has depressions or slots 34 on both its anterior and posterior face that mate with an insertion tool 66 (shown in FIGS. 11A & 11B). As shown in FIGS. 11B, 16C and 17C, projections 69 on the tips 67 of insertion tool 66 mate with scalloped depressions 81 within slots 34 to securely hold the implant during insertion. The implant has a pair of vertical through-channels 74 extending through the implant from the superior surface 28 to the inferior surface 30, which may be packed with bone graft and other bone growth inducing material prior to and/or after implantation to aid in spinal fusion. Preferably, the implant also has a chamfer 75 on both its superior and inferior surfaces 28, 30 at insertion end 79. As shown best in FIGS. 16D and 16E, chamfers 75 form a wedge-like shape at insertion end 79 to facilitate implant insertion through the transforaminal window. Chamfers 75 begin at a section of the implant at an angle β from the midline of the implant, where β may be in the range of 15° to 30° and preferably about 23°, and taper to the end of narrow insertion end 79. As shown in FIG. 16E, chamfers 75 form an angle γ with the vertical wall of narrow insertion end γ, where γ may be in the range of 50° to 80° and preferably about 60°.

Preferably, implant 22 also includes a beveled edge 76 along the perimeter of its superior and inferior surfaces 28, 30 As shown in FIG. 16B, beveled edge 76 may be beveled at an angle α to the vertical axis, which may be in the range of 25° to 45° and preferably about 37°. Beveled edge 76 is free from teeth 32 and both facilitates implant insertion and handling of the implant by physicians. Since edges 76 are free from teeth 32, the perimeter edges of the implant are unlikely to become snagged by tissue during implant insertion and a surgeon is less likely to tear protective gloves while handling the implant prior to and during insertion.

Figure 18:
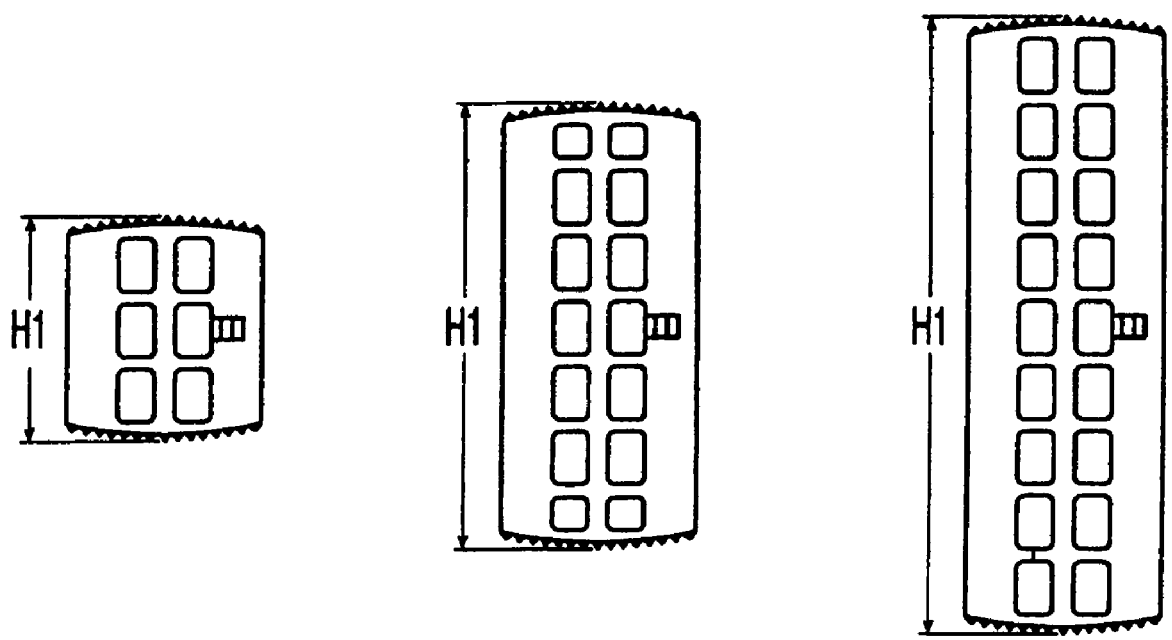
FIG. 18 is a side view of another preferred embodiment of the implant of the present invention.

As shown in FIG. 16C, in a preferred embodiment, the thickness of the walls T1 on the anterior and posterior sides of vertical through-channels 74 is greater than the width W1 of vertical through-channel 74. For example, for an implant with walls of equal thickness, T1 may be in the range of 3.4 to 4.0 mm and preferably about 3.5 mm and W1 may be on the order of 3.2 to 2.0 mm. The total implant width may be in the range of 9 to 11 mm, and preferably about 10 mm. It should be emphasized that the implant shown in FIGS. 16A–16C has walls 82 of equal thickness T1 on either side of channel 74, but in other embodiments walls 82 may have different thicknesses. Channels 74 may have an arcuate shape or any other suitable shape, e.g., rectangular, circular, etc. The implant may be formed of a radiolucent material selected from the polyaryl ether ketone family (PAEK), such as polyether ether ketone (PEEK) or polyether ketone ketone (PEKK), and may include radiopaque markers, such as pins 77, that act as radiographic markers to aid in positioning and monitoring the position of the implant. Preferably, radiopaque pins 77 extend substantially through the height of the implant so that postoperative spinal scans indicate the size of the implant used in a given patient. For example, a radiolucent implant with a 7.0 mm height includes radiopaque pins on the order of 6.0 mm in length, while a 17.0 mm implant has pins on the order of 16.0 mm in length. Pins 77 thus enable a physician to better evaluate a postoperative patient and monitor the position of the implant. Pins 77 may also function as fasteners for implants formed of two or more pieces. The implant may also be formed of a suitable biocompatible material such as titanium. As shown in FIG. 18, the implant may be formed of a stack of units to create an implant with a varying heights H1 ranging from about 7.0 mm to about 88.0 mm.

In still another embodiment shown in FIGS. 17A–17E, in addition to vertical through-channels 74, the implant has two horizontal through-channels 78 extending through the implant from anterior face 24 to posterior face 26. Channels 78 may have a width W2 in the range of 2.5 to 7.5 mm and preferably about 5.0 mm, and a radius of curvature R4 in the range of 1.0 to 2.0 mm and preferably about 1.2 mm. The implant may also have at least one lateral horizontal through-channel 80 extending from a narrow end 25 toward an adjacent anterior-posterior horizontal through-channel 78. Lateral through channel 80 may have a width W3 in the range of 2.0 to 5.0 mm and preferably about 3.0 mm, and a radius of curvature R5 in the range of 1.0 to 2.0 mm and preferably about 1.2 mm. Preferably, the implant has lateral horizontal through-channels 80 at both narrow ends 25. Alternatively, a single lateral horizontal through channel may extend from one narrow end 25 completely through the implant to the other narrow end 25. Wall 84 between horizontal through-channels 78 may have a thickness in the range of 2.0 to 4.0 mm and preferably about 2.2 mm. Channels 78, 80 may be rectangular, trapezoidal or circular in shape, and may be packed with bone graft or other bone growth inducing material before and after implant insertion to aid in spinal fusion.

Figure 4:
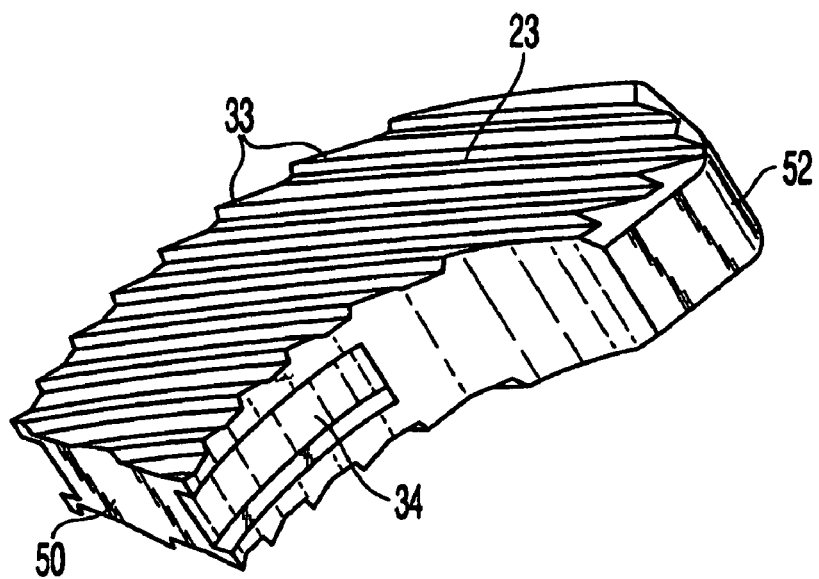
FIG. 4 is a perspective view of still another embodiment of the implant of the present invention.
Figure 5:
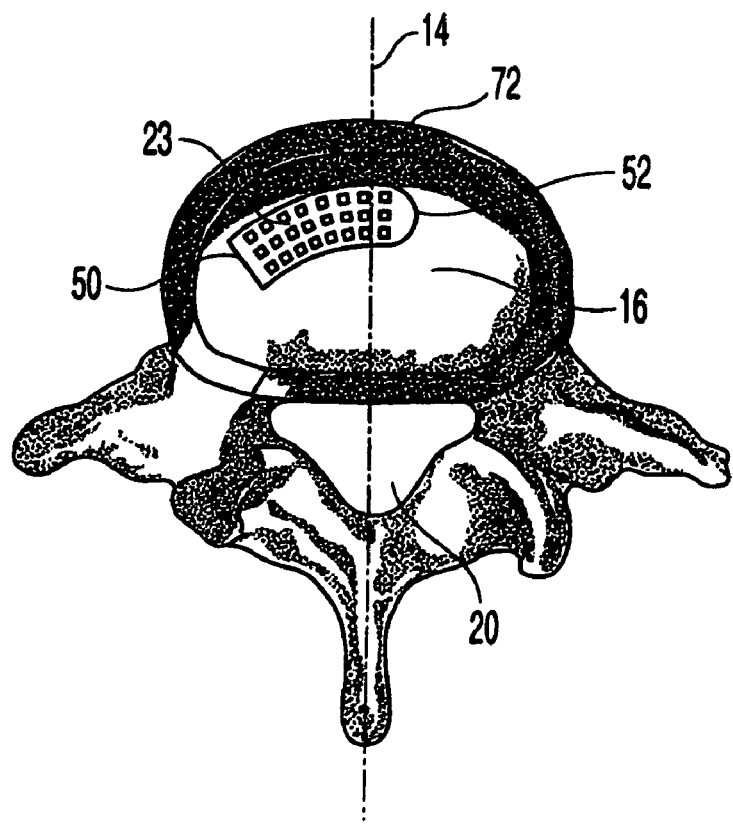
FIG. 5 is an axial view of a typical human vertebrae showing the implant of FIG. 4 in an asymmetric final position.

Reference is now made to FIG. 4 which is a perspective view of another embodiment an implant. As in the previous embodiment, implant 23 has a curved body with substantially parallel arcuate anterior and posterior faces 24, 26, convex superior and inferior surfaces 28, 30 contributing to a tapering thickness 31, and channels 34 for engaging a surgical instrument, such as an insertion tool. In this embodiment, implant 23 has a substantially straight or blunted narrow end 50 and a curved narrow end 52 separating parallel, arcuate anterior and posterior faces 24, 26. As shown in FIG. 5, the final position of implant 23 in disc space 16 may be asymmetric with respect to midline 14 of the patient's spine. The final position of implant 22 may also be asymmetric with respect to the midline of the spine.

Figure 6:
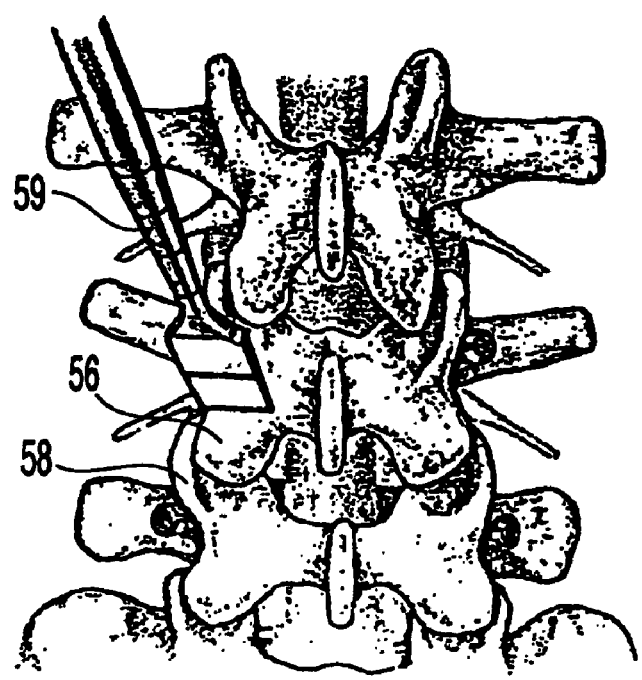
FIG. 6 is a posterior view of a section of human spine prior to preparation of the transforaminal window.
Figure 7:
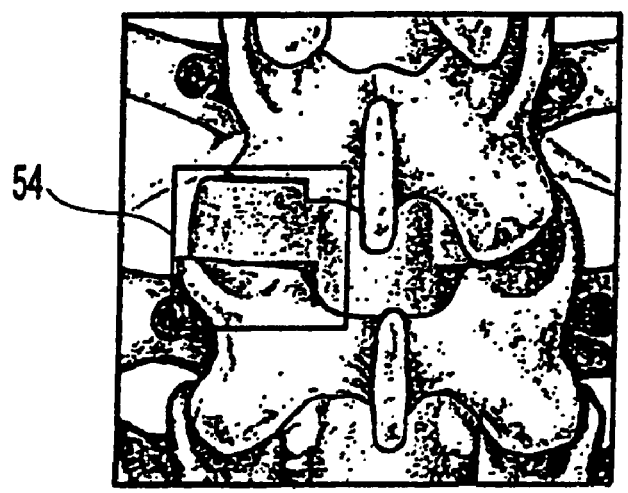
FIG. 7 is a posterior view of a section of human spine with the transforaminal window prepared.
Figure 8A:
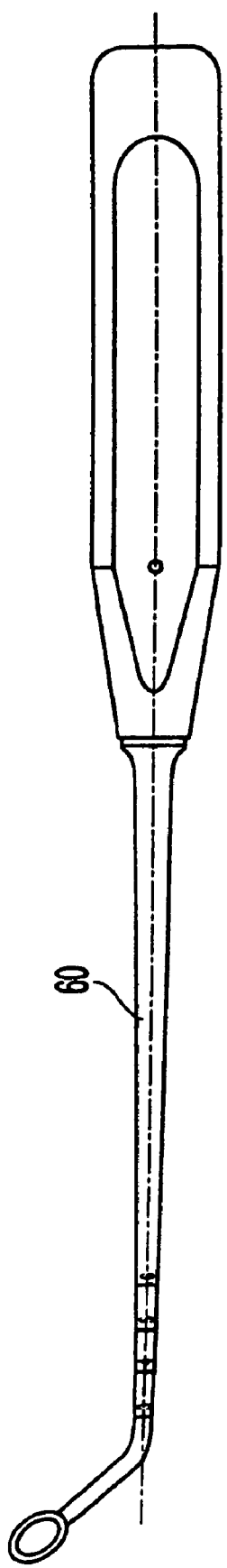
FIG. 8A depicts an angled bone curette for use during the T-PLIF procedure.
Figure 8B:
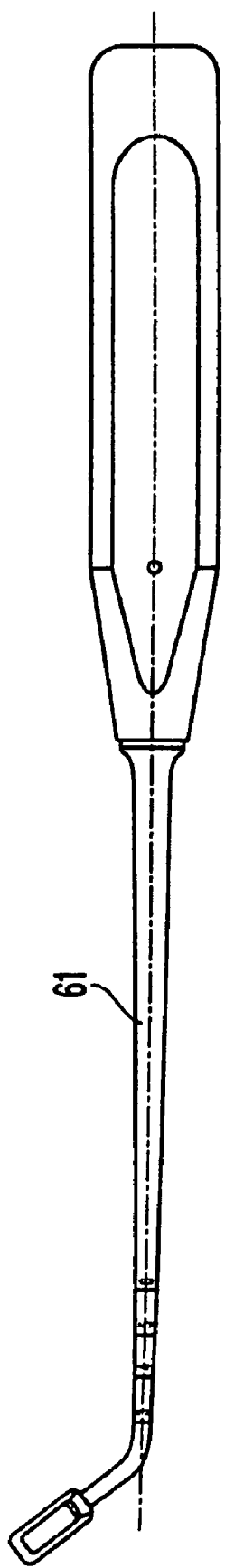
FIG. 8B depicts another angled bone curette for use during the T-PLIF procedure.
Figure 8C:
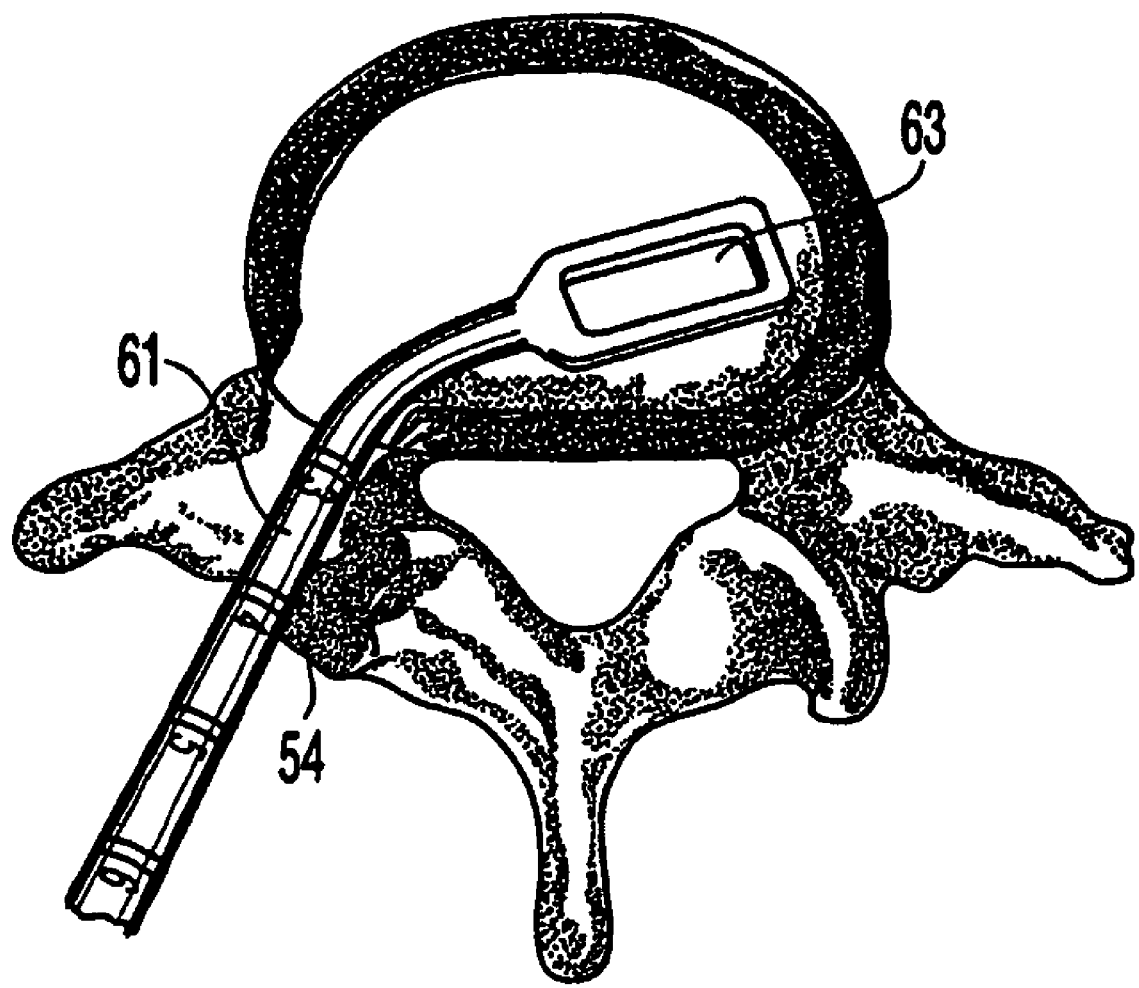
FIG. 8C depicts an angled bone curette removing disc material from an affected disc space.

As shown in FIGS. 2A, 3A, 16C, 17C and FIG. 11D, the rocker-like shape of implant 22 enables the surgeon to insert the implant through the narrow transforaminal window, typically on the range of about 9.0 to 15.0 mm wide, and seat the implant in the disc space anteriorly of the dura without disturbing the anterior curtain of the disc space. The typical surgical technique for the T-PLIF procedure begins with the patient being placed in a prone position on a lumbar frame. Prior to incision, radiographic equipment can assist in locating the precise intraoperative position of the T-PLIF implant. Following incision, the facets, lamina and other anatomical landmarks are identified. The affected vertebrae are distracted using a lamina spreader or a lateral distractor, both of which are commonly known in the art. In the latter case, screws may be inserted through the pedicles into the vertebrae to interface with the lateral distractor. As shown in FIGS. 6 & 7, following distraction, the transforaminal window 54 is created by removing the inferior facet 56 of the cranial vertebrae and the superior facet 58 of the caudal vertebrae using one or more osteotomes 59 and/or automatic burrs (not shown) of different sizes. A discectomy is performed during which disc material from the affected disc space may be removed using a combination of straight and angled curettes. Angled curettes, which may be configured with rounded profile 60 (FIG. 8A) or a rectangular profile 61 (FIG. 8B), enable removal of material on the far side 63 of the disc space opposite transforaminal window 54, as shown in FIGS. 8C.

Figure 10A:
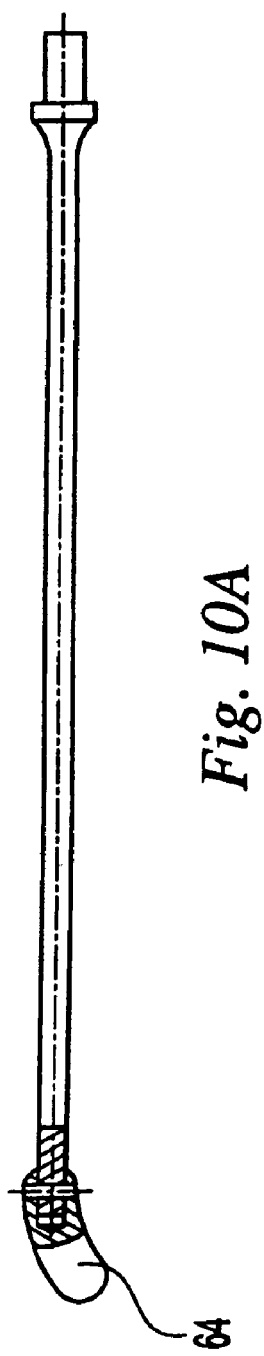
FIG. 10A depicts a trial-fit spacer for use during a T-PLIF procedure.
Figure 10B:
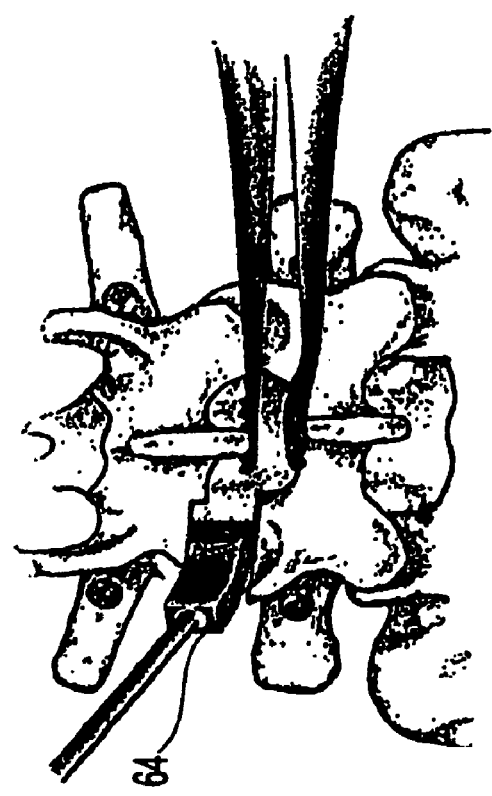
FIG. 10B depicts a trial-fit spacer being inserted into an affected disc space via a transforaminal window.

After the discectomy is complete, the superficial layers of the entire cartilaginous endplates are removed with a combination of straight and angled bone rasps. As shown in FIGS. 9A and 9B, angled rasps 62 may be angled to reach far side 63 of the disc space opposite transforaminal window 54. Rasps 62 expose bleeding bone, but care should be taken to avoid excess removal of subchondral bone, as this may weaken the anterior column. Entire removal of the endplate may result in subsidence and loss of segmental stability. Next, an appropriately sized trial-fit T-PLIF spacer/template 64, shown in FIGS. 10A and 10B, may be inserted into the intervertebral disc space using gentle impaction to determine the appropriate implant thickness for the disc space to be filled. Fluoroscopy can assist in confirming the fit of the trial spacer. If the trial spacer 64 appears too loose/too tight, the next larger/smaller size trial spacer should be used until the most secure fit is achieved. For example, if a trial fit spacer with a maximum thickness of 11 mm is too loose when inserted into the disc space, a physician should try the 13 mm thick spacer, and so on. Trial fit spacers preferably range in height from about 7 mm to about 17 mm.

Figure 11C:
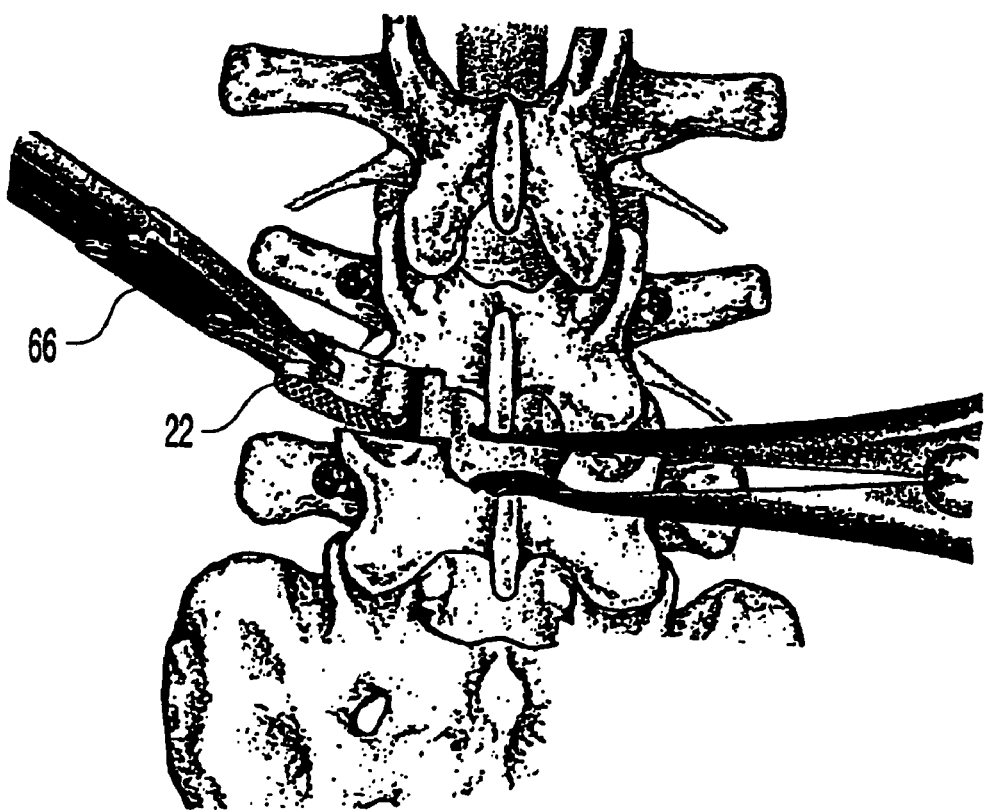
FIG. 11C depicts an posterior view of the human spine showing a T-PLIF implant being inserted with an implant holder.
Figure 11D:
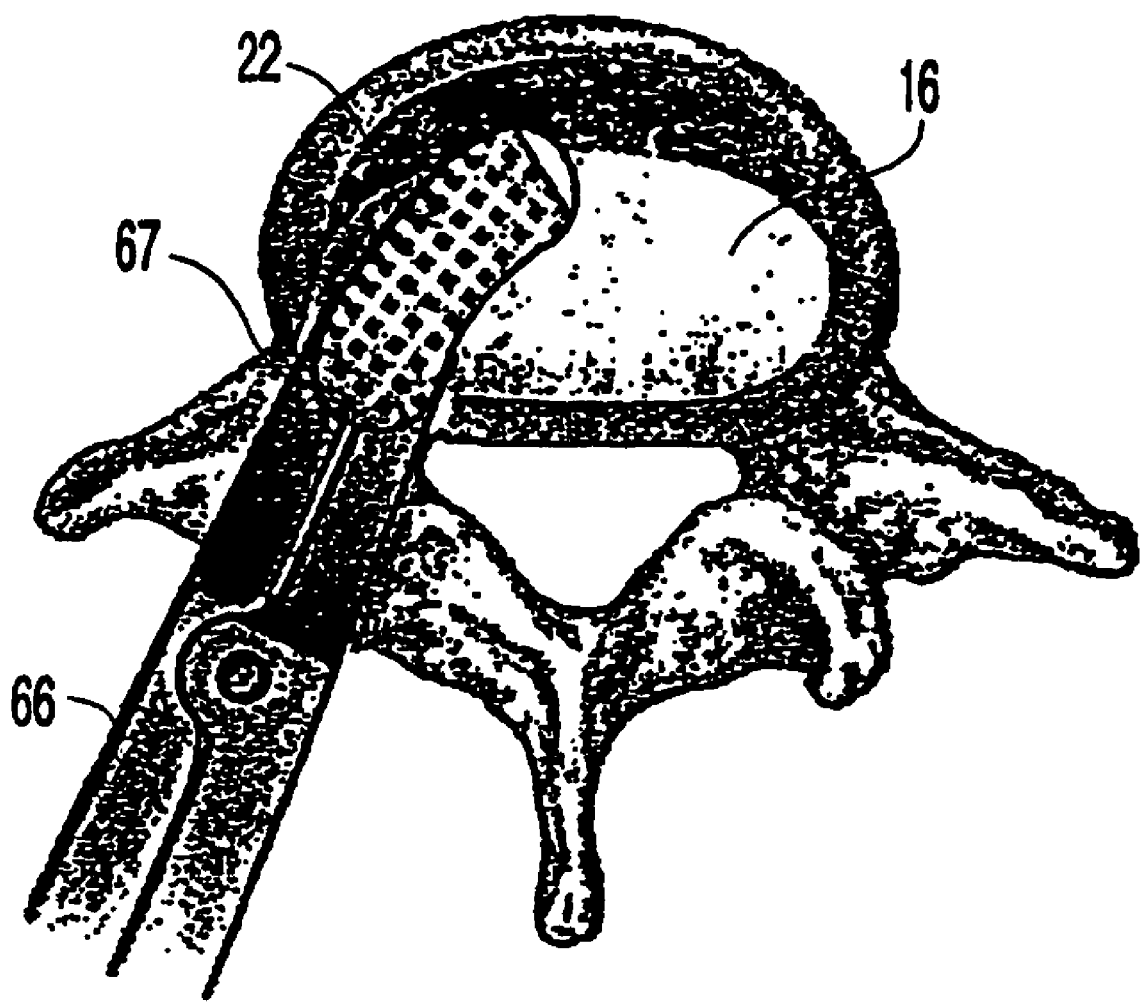
FIG. 11D depicts a top view of a human vertebrae showing a T-PLIF implant being inserted with in an implant holder.
Figure 12:
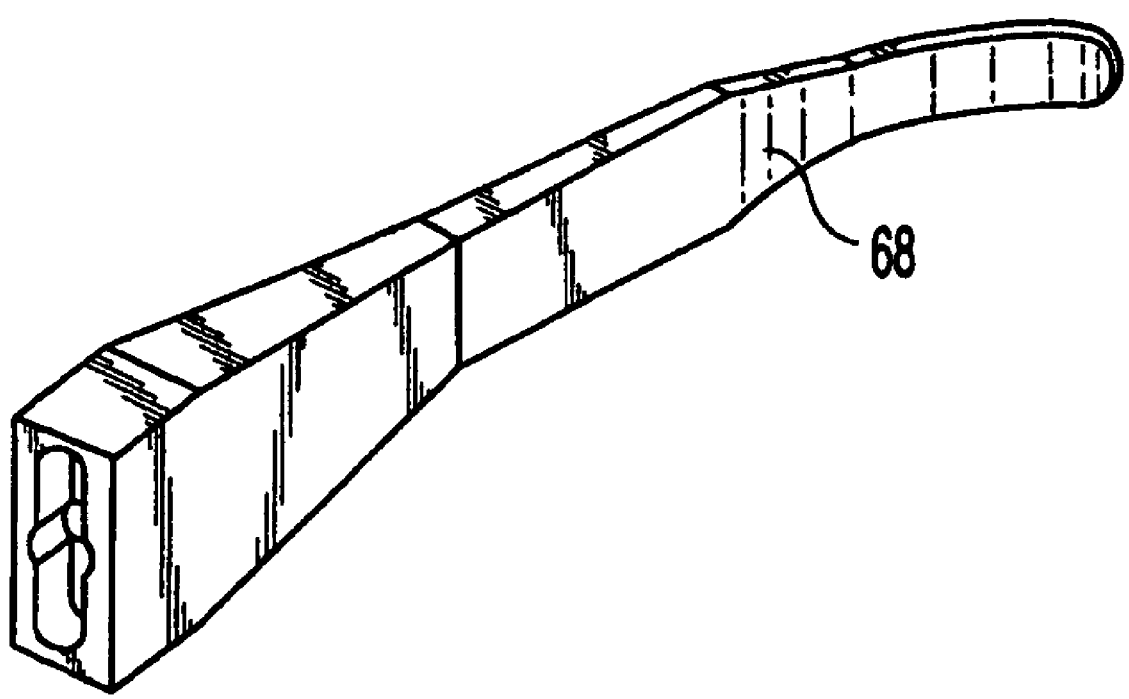
FIG. 12 depicts an implant guide tool for use with the T-PLIF implant.
Figure 13A:
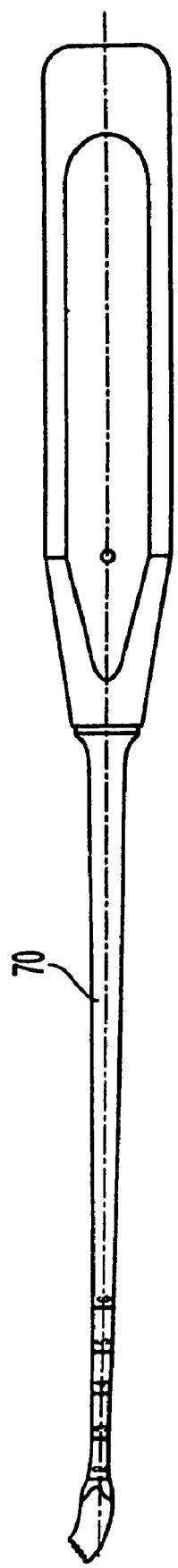
FIG. 13A depicts an angled impactor tool for use with the T-PLIF implant.
Figure 13B:
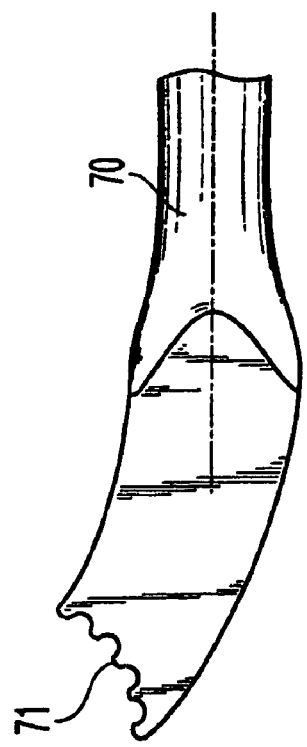
FIG. 13B is a close-up view of the tip of the impactor tool shown in FIG. 13A.
Figure 14:
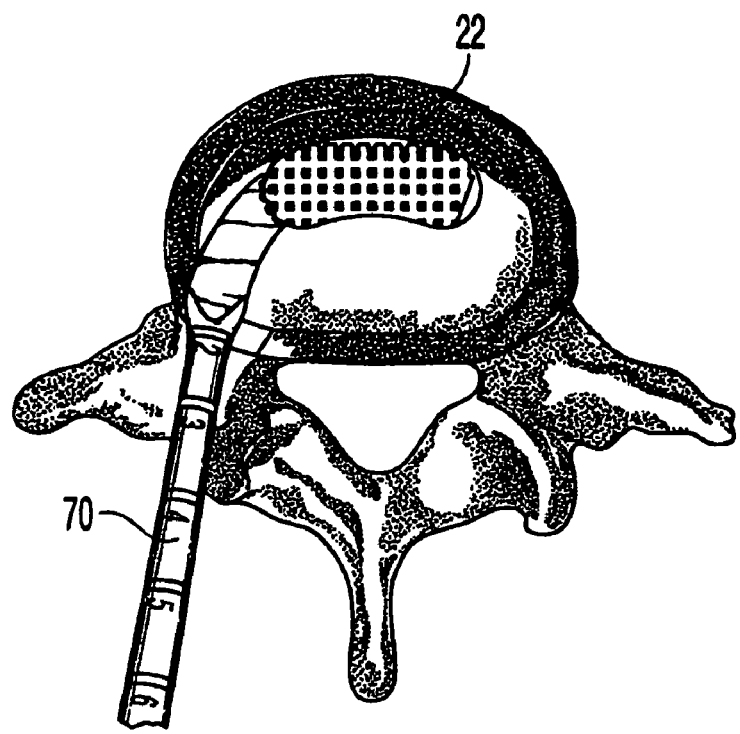
FIG. 14 is a top view of a typical human vertebrae showing an implant according to the present invention being properly positioned into an affected disc space using the impactor tool shown in FIG. 13A.

Upon identifying and removing the best fitting trial spacer, a T-PLIF implant of appropriate size is selected. At this time, prior to placement of the T-PLIF implant, bone graft material, such as autogenous cancellous bone or a bone substitute, may be placed in the anterior and lateral aspect of the affected disc space. Channels in implant 22 may also be packed with bone graft material prior to insertion. As shown in FIGS. 11C and 11D, T-PLIF implant 22 is then held securely using a surgical instrument such as implant holder 66 (shown more clearly in FIG. 11A), which engages the channels or slots 34 at one end of implant 22. The tips 67 of implant holder 66 may be curved or angled to mate with curved implant 22 and facilitate insertion of implant 22 into disc space 16. T-PLIF implant 22 is then introduced into the intervertebral disc space 16 via the transforaminal window, as shown in FIG. 11C. A guide tool having a curved blade 68 (shown in FIG. 12) to match the curvature of the anterior face of implant 22 may be used to properly guide the implant into affected disc space 16. The implant may be guided along an arcuate path to its final position. Slight impaction may be necessary using implant holder 66 (shown in FIG. 11A) or an impactor tool 70 (shown in FIG. 13A) to fully seat the implant. As shown in FIGS. 13A & 13B, impactor tool 70 may also be curved or angled to facilitate seating of the implant through the narrow transforaminal window. Also, the face 71 of impactor 70 may be concavely shaped to mate with the end of implant 22, as shown in FIG. 14.

Figure 15:
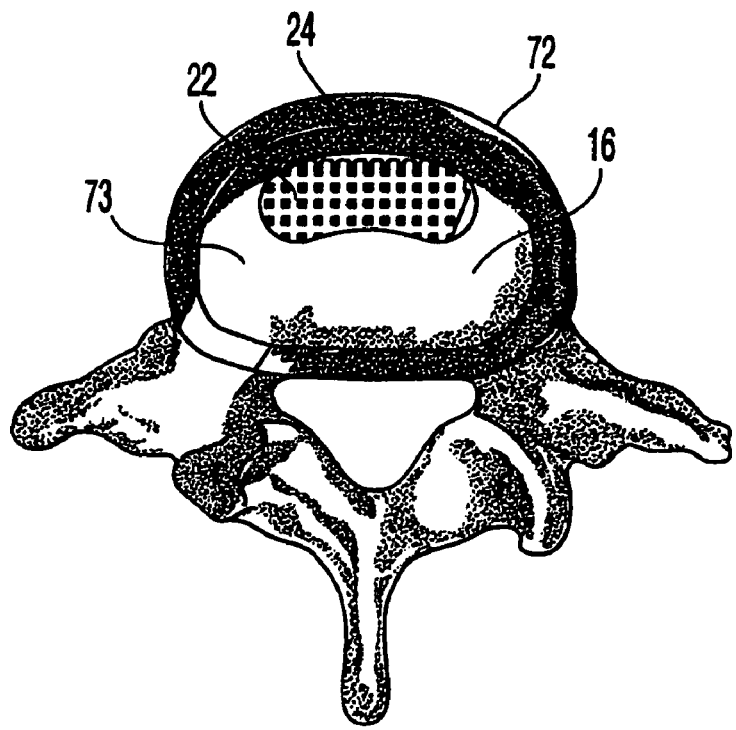
FIG. 15 is a top view of the vertebrae of FIG. 1 showing the T-PLIF implant in a final position.

Once the T-PLIF implant is in the desired final position, such as the symmetric final position shown in FIG. 15 or the asymmetric position shown in FIG. 5, implant holder 66, and possibly guide tool 68, is removed and additional bone graft material 73 may be inserted into the disc space and/or the channels 74, 78 and 80 of the implant. Preferably, T-PLIF implant 22 is slightly recessed from the anterior edge 72 of the vertebral body, but implanted in the anterior-most third of the disc space such that the implant is closer to the anterior edge 72 of the disc space than the posterior edge. As shown in FIG. 15, the curvature of anterior face 24 of implant 22 is substantially the same as the curvature of anterior edge 72 of disc space 16. In the symmetric seated position shown in FIG. 15, a single T-PLIF implant 22 provides balanced support to the spinal column about the midline of the spine.

While certain preferred embodiments of the implant have been described and explained, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An intervertebral implant for posterior insertion via a transforaminal window comprising;
   curved, substantially parallel posterior and anterior faces, the posterior and anterior faces extending along a longitudinal axis of the implant;
   a pair of convex narrow ends separating the posterior and anterior faces;
   superior and inferior faces for contacting upper and lower vertebral endplates, the superior and inferior faces defining a thickness of the implant;
   at least one depression in the anterior or posterior face for engagement by an insertion tool;
   at least two vertical through-channels extending through the implant from the superior face to the inferior face, each vertical through-channel having a width and walls on posterior and anterior sides of the width, the walls on the posterior and anterior sides of the width of the vertical through-channels having a thickness greater than the width of the vertical through channels; and
   a chamfer on the superior and inferior faces at one of the convex narrow ends to facilitate implant insertion.

2. The implant of claim 1, wherein a first convex narrow end is configured and adapted to be inserted first into an affected disc space before a second convex narrow end, and the chamfer is at the first convex narrow end.

3. The implant of claim 2, further comprising a beveled edge along a perimeter of the superior and inferior faces.

4. The implant of claim 3, further comprising at least two anterior-posterior horizontal through-channels extending through the implant from the posterior face to the anterior face.

5. The implant of claim 4, further comprising at least one lateral horizontal through-channel extending through the implant from at least one of the convex narrows ends to an adjacent anterior-posterior horizontal through channel.

6. The implant of claim 3, further comprising a plurality of bone-engaging undulating surfaces on the superior and inferior faces.

7. The implant of claim 6, wherein the undulating surfaces are teeth.

8. The implant of claim 1, wherein the width of the vertical through-channels in the anterior-posterior direction is approximately 3.0 mm and the thickness of the walls on the posterior and anterior sides of the vertical through-channels is approximately 3.5 mm.

9. The implant of claim 3, wherein the superior and inferior faces are convex.

10. The implant of claim 9, wherein the thickness of the implant between the superior and inferior faces is greatest at a mid-section between the narrow ends of the implant and the thickness tapers toward the narrow ends.

11. The implant of claim 3, wherein the implant is formed of polyaryl ether ketone (PAEK).

12. The implant of claim 3, wherein the implant is formed of polyether ether ketone (PEEK), polyether ketone ketone (PEKK), or titanium.

13. The implant of claim 1, further comprising one or more radiopaque markers extending substantially through the thickness of the implant.

14. The implant of claim 13, wherein the radiopaque markers indicate a size of the implant.

15. The implant of claim 1, wherein the implant is formed of a plurality of interconnecting bodies assembled to form a single unit.

16. The implant of claim 15, further comprising at least one pin extending through an opening in the plurality of bodies to hold the bodies together as a single unit.

17. The implant of claim 16, wherein the plurality of bodies have mating interlocking surfaces that aid in holding the bodies together as a single unit.

18. An intervertebral implant comprising:
   a body having a posterior face, an anterior face, a pair of curved ends separating the posterior and anterior faces, and superior and inferior faces for contacting upper and lower vertebral endplates, the superior and inferior faces defining a thickness of the implant;
   wherein the body includes at least one vertical through-channel extending from the superior face to the inferior face, the vertical through-channel having a width and walls on posterior and anterior sides of the width, the walls on the posterior and anterior sides of the width of the vertical through-channel having a thickness greater than the width of the vertical through channel; and
   the anterior and posterior faces include at least one slot configured and adapted to mate with an insertion tool, wherein the slots each include at least one recess for engaging a corresponding projection formed on the insertion tool.

19. The implant of claim 18, further comprising a chamfer on the superior and inferior faces at one of the curved ends to facilitate implant insertion.

20. The implant of claim 18, further comprising a plurality of bone-engaging undulating surfaces on the superior and inferior faces.

* * * * *